United States Patent [19]

Doenges et al.

[11] Patent Number: 4,841,554
[45] Date of Patent: Jun. 20, 1989

[54] X-RAY SCANNER FOR INSPECTING ARTICLES MOVING THERETHROUGH

[75] Inventors: Gerhard Doenges, Heidenrod-Kemel; Rolf Dietrich, Hofheim; Helmut Thoma, Mainz; Eckart-Alfred Von Unger, Munich, all of Fed. Rep. of Germany

[73] Assignee: Heimann GmbH, Wiesbaden, Fed. Rep. of Germany

[21] Appl. No.: 161,991

[22] Filed: Feb. 29, 1988

[30] Foreign Application Priority Data

Mar. 11, 1987 [DE] Fed. Rep. of Germany ....... 8703674

[51] Int. Cl.$^4$ .......................................... G01N 23/04
[52] U.S. Cl. ...................................... 378/57; 378/62; 378/177; 378/195; 378/201; 250/359.1
[58] Field of Search ................... 378/57, 62, 177, 195, 378/201, 208; 250/359.1

[56] References Cited

U.S. PATENT DOCUMENTS

| | | | |
|---|---|---|---|
| 2,179,859 | 11/1939 | Page | 378/57 |
| 3,488,495 | 1/1970 | Schneeman | 378/195 |
| 3,768,645 | 10/1973 | Conway et al. | 250/359.1 |
| 3,980,889 | 9/1976 | Haas et al. | 378/57 |
| 4,020,346 | 4/1977 | Dennis | 378/57 |
| 4,239,969 | 12/1980 | Haas et al. | 378/57 |
| 4,301,366 | 11/1981 | Bertin et al. | 250/359.1 |
| 4,366,382 | 12/1982 | Kotowski | 378/57 |
| 4,644,578 | 2/1987 | Paolini | 378/57 |
| 4,695,729 | 9/1987 | Monno et al. | 378/59 |
| 4,722,096 | 1/1988 | Dietrich et al. | 378/57 |

FOREIGN PATENT DOCUMENTS 0247491 12/1987 European Pat. Off. .............. 378/57

*Primary Examiner*—Janice A. Howell
*Assistant Examiner*—John C. Freeman

[57] ABSTRACT

An x-ray scanner for inspecting articles moving therethrough, such as on a conveyor, has a frame on which an x-ray source, a collimator for the x-ray beam, and a radiation detector are mounted. The frame resists flexural and torsional stresses so as to maintain the relative positions of the x-ray source, the collimator, and the radiation receiver in the presence of such stresses. The scanner is mounted in a rack in which the frame is seated by a resilient support. The conveyor which is used to move articles through the x-ray beam between the x-ray source and the radiation receiver is supported by the rack, so that mechanical stresses to the conveyor, such as the placement of heavy articles thereon, are not conveyed to the frame, and therefore do not disturb the alignment of the components mounted on the frame, due to the intervention of the resilient support.

2 Claims, 1 Drawing Sheet

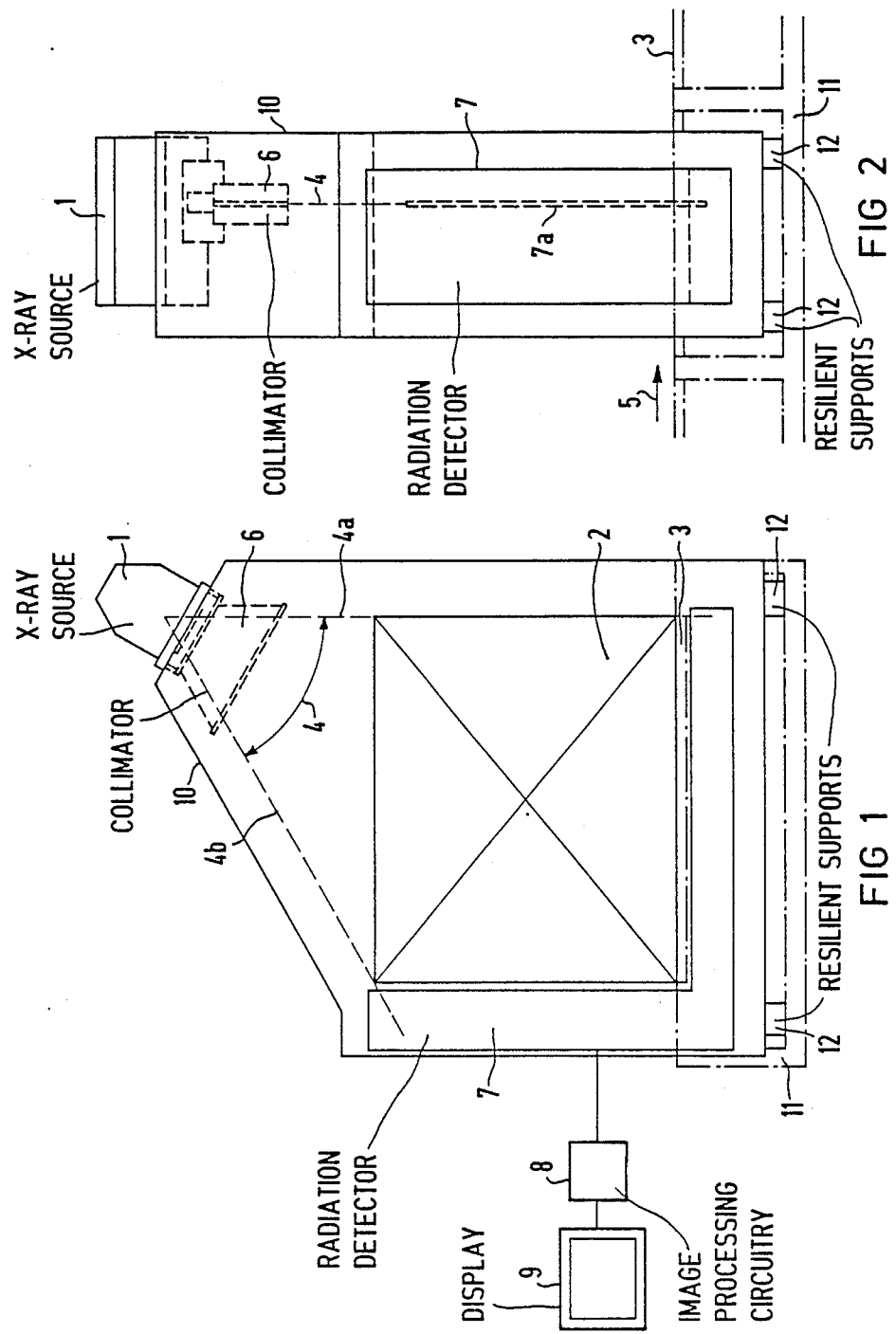

X-RAY SCANNER FOR INSPECTING ARTICLES MOVING THERETHROUGH

BACKGROUND OF THE INVENTION

1. Field of the Invention

The present invention is directed to x-ray scanners of the type through which articles are conveyed for inspection thereof by an x-ray beam.

2. Description of the Prior Art

X-ray scanners are known in the art having an x-ray source with a collimator for generating a fan-shaped x-ray beam through which an article to be inspected is moved, with radiation attenuated by the article being detected at a radiation detector on the opposite side of the conveyor. Image processing electronics are provided for constructing a visual image from the attenuated radiation signal. Scanners of this type are used, for example, to inspect baggage.

The radiation receiver may be formed by a row of individual detectors which supply the acquired values in parallel. These values correspond to the attenuated radiation intensity, and are entered in an image memory. A continuous image is then constructed for display on a monitor based on the content of the image memory.

In x-ray scanners of this type, the quality of the signals generated by the radiation detector (or receiver) is critically dependent on the exact adjustment of the fan-shaped x-ray beam. To this end, an exact geometrical configuration of the focus of the x-ray source, the collimator, and the radiation receiver is crucial. To limit the radiation dose and the scatter radiation to a minimum, a optimally thin fan beam is desired. Thus the collimator in such scanners generally has a small column width in the range of a few tenths of a milllimeter. The radiation receiver is thus irradiated by a beam which has a width of about three millimeters, in accord with the relevant geometrical conditions (the spacing between the beam focus and the collimator, and between the collimator and the radiation receiver). The components are geometrically arranged so that the effective surface of the radiation receiver and the area of the incident radiation are substantially coincident. A precise adjustment must be undertaken to achieve this result, particularly given the use of radiation receivers which are in the form of angled detector rows.

Due to the movement of the conveyor means during operation as well as due to the placement of articles thereon, and particularly given the use of scanners of this type in vehicles as a mobile x-ray scanner, the x-ray scanner is subjected to jolts and vibrations to a considerable degree. It is therefore difficult to maintain the necessary precise adjustment of the components during operation as a result of such mechanical stresses.

SUMMARY OF THE INVENTION

It is an object of the present invention to provide an x-ray scanner of the type described above wherein the risk of mis-adjustment of the beam focus, the beam collimator and the radiation receiver during operation of the scanner is reduced.

The above object is achieved in accordance with the principles of the present invention in an x-ray scanner wherein the x-ray source, the collimator and the radiation receiver are mounted to a common frame which is flexurally and torsionally stiff, i.e., the frame is resistant to flexural and torsional forces. The frame is resiliently seated in the rack in which the scanner is mounted. The rack may also support the conveyor means which moves the articles to be inspected through the scanner, however, due to the resilient seating of the frame, the frame, and the components mounted thereon, will be mechanically insulated from jolts and vibrations which may arise due to the normal operation of the conveyor, or due to the placement of articles thereon. The frame is also insulated from external jolts to the scanner as a result of the resilient seating.

In one embodiment of the invention, the collimator and the x-ray source are individually mounted to the frame. The exact geometrical relationship of the collimator to the radiation receiver is preserved when the scanner is replaced for service. When the scanner is placed back in service, only the position of the x-ray source must be re-adjusted, which is a relatively simple procedure.

DESCRIPTION OF THE DRAWINGS

FIG. 1 is an end view of an x-ray scanner constructed in accordance with the principles of the present invention, with electronic signal processing components being schematically illustrated.

FIG. 2 is a side view of the scanner of FIG. 1.

DESCRIPTION OF THE PREFERRED EMBODIMENTS

As shown in the drawings, an x-ray scanner constructed in accordance with the principles of the present invention includes an x-ray source 1 which generates a fan-shaped x-ray beam 4 in combination with a collimator 6, consisting of lead plates. The fan-shaped x-ray beam 4 transradiates a series of articles 2 being inspected. The articles 2 are moved through the fan-shaped x-ray beam on a conveyor belt 3. The conveyor belt 3 moves in the direction of the arrow 5 shown in FIG. 2, and the fan-shaped x-ray beam 4 is in a plane perpendicular to the direction of movement of the conveyor belt 3. The edge or boundary rays of the x-ray beam 4 are referenced 4a and 4b.

Radiation attenuated by the articles 2 being inspected is incident on an angled radiation receiver 7 consisting of a plurality of individual detectors mounted in a housing. The output signals from the detectors are supplied via conventional processing electronics 8 to a monitor 9 on which an image of the article 2 is displayed. The range of signal acquisition or coverage for the radiation within the radiation receiver 7 is referenced 7a in FIG. 2.

The x-ray source 1, the radiation receiver 7 and the collimator 6 are mounted to a common frame 10 which is resistant to flexural and torsional stresses. The frame 10 is resiliently seated in the mounting rack 11 for the x-ray scanner by resilient supports 12. The resilient supports 12 insulate the frame 10 from mechanical vibrations and jolts caused by the usual operation of the conveyor belt 3 moving through the scanner, as well as by the placement of articles 2 on the conveyor belt 3. The resilient supports 12 also insulate the frame 10 from external jolts to the scanner 12.

The resilient support 12 are thus of the type which do not transmit forces between the components connected by those supports, and thus exclude screws, rivets, welds and other types of conventional, rigid connections. A commercially available component suitable for use as the resilient supports 12 is a rubber-metal buffer manufactured by Gummi-Metall-Technik GmbH of West Germany, this component generally consisting of two metal plates or faces with a compressible rubber member therebetween.

The radiation receiver 7 is of conventional design and structure, and may consist, for example, of an angled row of a plurality of individual detectors, each detector being formed by a scintillation crystal and a following photodiode.

The collimator 6 and the x-ray source 1 may be individually mounted to the frame 10, i.e., the collimator 6 and the x-ray source 1 need not be removed from the frame 10 as a unit. This permits the x-ray source 1 to be removed and serviced by itself, without disturbing the geometrical alignment of the collimator 6 with respect to the radiation receiver 7.

Although modifications and changes may be suggested by those skilled in the art it is the intention of the inventors to embody within the patent warranted hereon all changes and modifications as reasonably and properly come within the scope of their contribution to the art.

We claim as our invention:

1. An x-ray scanner comprising:
   an x-ray source which generates an x-ray beam emanating from a focus;
   a collimator disposed with respect to said x-ray source for collimating said x-ray beam to generate a fan-shaped x-ray beam;
   means for conveying a series of articles to be inspected through said fan-shaped x-ray beam;
   a radiation detector disposed for receiving radiation from said x-ray beam attenuated by said articles and generating electrical signals corresponding to the intensity of the received radiation;
   means for generating a visual image of said articles based on said signals;
   a rack on which at least said means for conveying is mounted;
   a frame to which said x-ray source, said collimator and said radiation receiver are mounted, said frame being resistant to flexural and torsional stresses; and
   resilient means disposed between said frame and said rack for mounting said frame to said rack to substantially insulate said frame and the components mounted thereon from mechanical stresses caused by the operation of said means for conveying.

2. An x-ray scanner as claimed in claim 1, further comprising means for individually mounting said collimator and said x-ray source to said frame.

* * * * *